United States Patent [19]

Shirkhanzadeh

[11] Patent Number: 5,383,935
[45] Date of Patent: Jan. 24, 1995

[54] PROSTHETIC IMPLANT WITH SELF-GENERATED CURRENT FOR EARLY FIXATION IN SKELETAL BONE

[76] Inventor: Morteza Shirkhanzadeh, 64 Ontario Street, Apt. 410, Kingston, Ontario, Canada, K7L 5J4

[21] Appl. No.: 127,491

[22] Filed: Sep. 28, 1993

[51] Int. Cl.⁶ .................... A61F 2/28; A61F 2/02; A61F 2/30; A61F 2/54
[52] U.S. Cl. ..................... 623/16; 623/11; 623/18; 623/66; 433/173; 433/174
[58] Field of Search .............. 623/11, 16, 18, 66; 433/173, 174

[56] References Cited

U.S. PATENT DOCUMENTS

| | | | |
|---|---|---|---|
| 3,842,841 | 10/1974 | Brighton et al. | 128/419 R |
| 3,897,267 | 7/1975 | Tseung et al. | 136/86 A |
| 4,027,392 | 6/1977 | Sawyer et al. | 433/174 |
| 4,175,565 | 11/1979 | Chiarenza et al. | 433/174 |
| 4,336,617 | 6/1982 | Shikita et al. | 623/16 |
| 4,506,674 | 3/1985 | Brighton et al. | 128/419 F |
| 4,846,837 | 7/1989 | Kurze et al. | 623/16 |
| 5,205,921 | 4/1993 | Shirkanzadeh | 623/16 X |
| 5,258,044 | 11/1993 | Lee | 623/16 |

FOREIGN PATENT DOCUMENTS 2518397  6/1983  France ..................... 433/173

Primary Examiner—Randall L. Green
Assistant Examiner—Dinh X. Nguyen

[57] ABSTRACT

A prosthetic implant for implantation into skeletal bone comprising an implantable base member having an internal housing surrounded partially by a porous wall, an anode secured in the internal housing in electrical contact with the porous wall, and a porous means placed in the internal housing for retaining a biocompatible electrolyte. When implanted into bone structure, the prosthetic implant generates sufficient current flow which results in invivo formation of calcium phosphate minerals between the implant and the surrounding bone, thereby, resulting in improved fixation and stability of the implant.

16 Claims, 2 Drawing Sheets

FIG·1
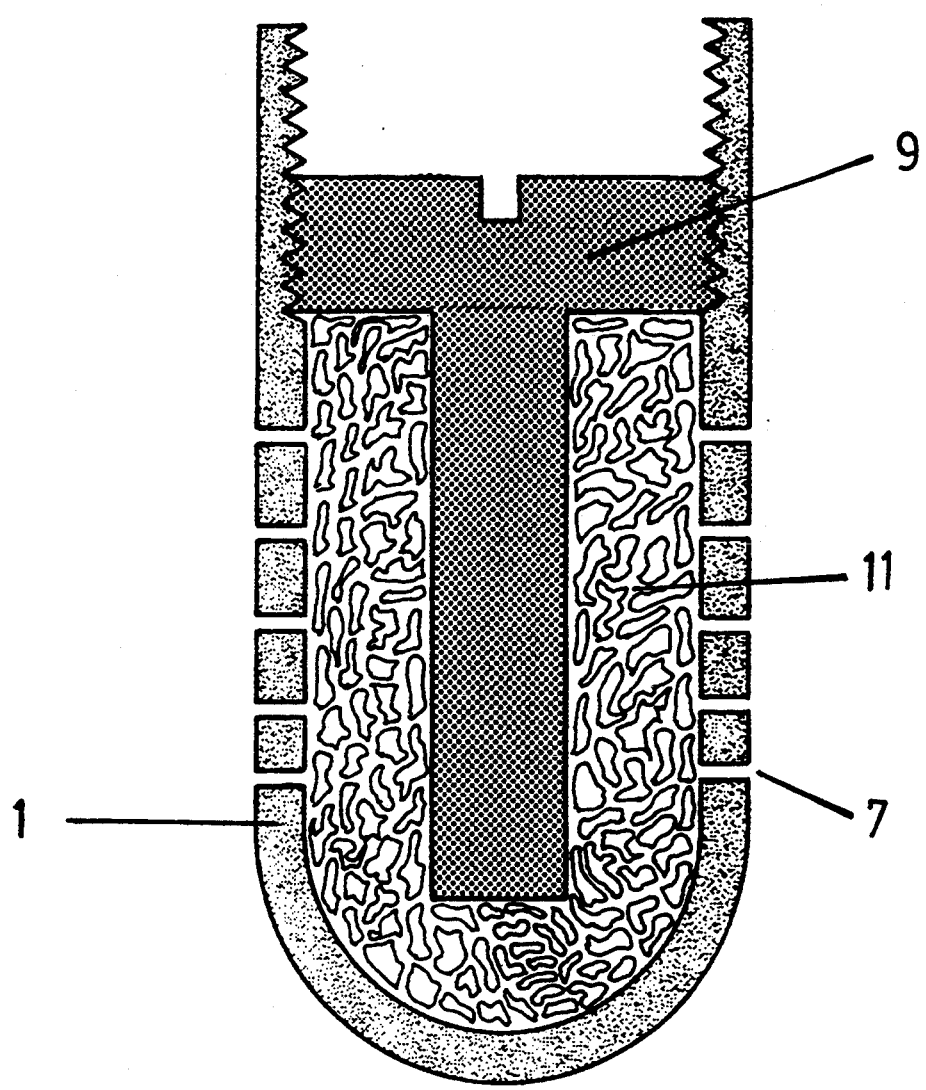

FIG·2
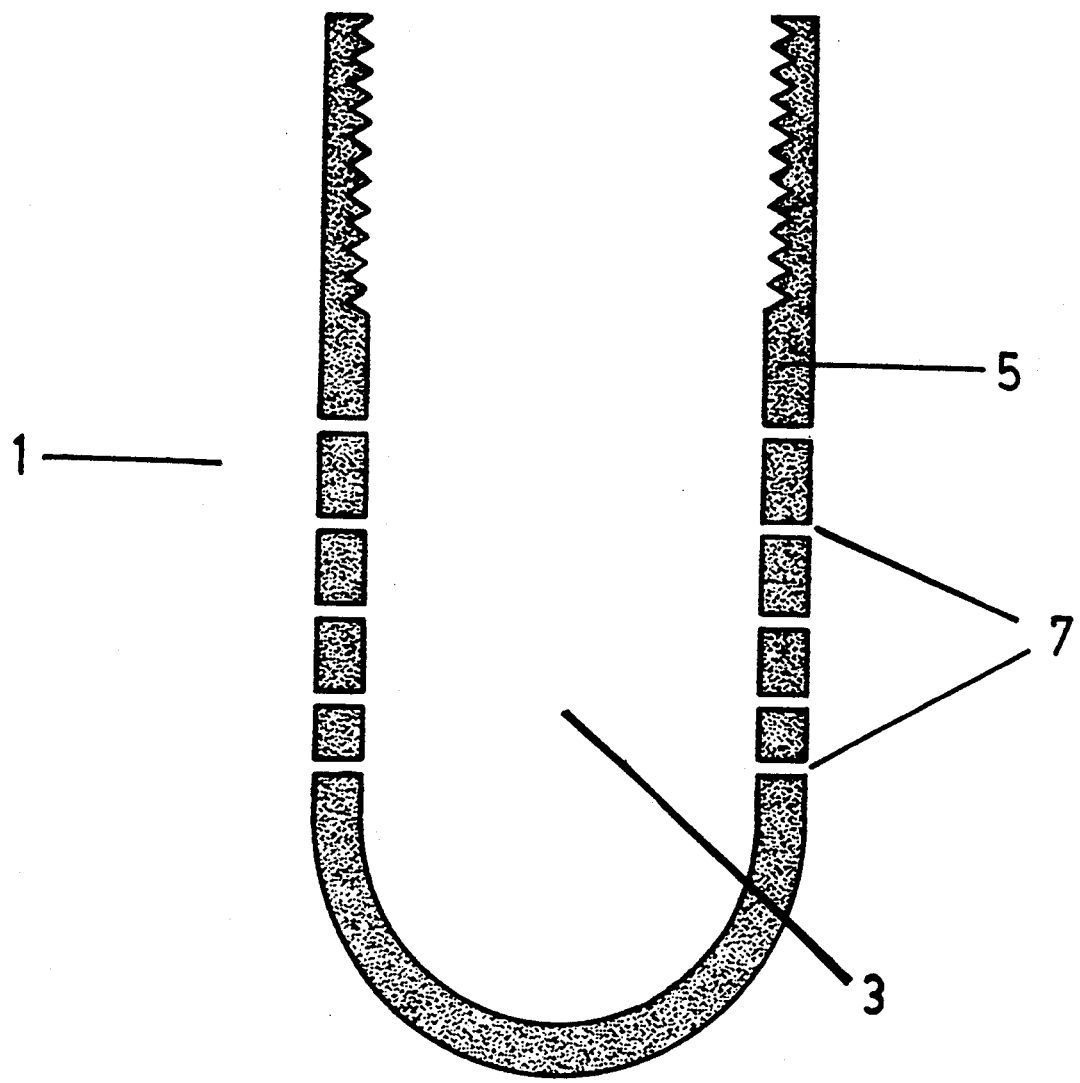

PROSTHETIC IMPLANT WITH SELF-GENERATED CURRENT FOR EARLY FIXATION IN SKELETAL BONE

BACKGROUND OF THE INVENTION

1. Field of the Invention

The invention relates to medical prostheses for implantation in a body, and more particularly, to prostheses which are intended to be fixed into the skeletal structures, such as dental implants and hip joint prostheses.

2. Description of the Prior Art

Medical implants such as dental implants and joint prostheses are normally implanted into the skeletal structure of humans to replace missing or damaged skeletal parts. Often, it is intended that these implants become a permanent part of the skeletal structure. It is important, therefore, that the metal implant be strongly fixed to the skeletal bone structure. Traditional problems, in implant placement and post-operative instability, have been associated with inability to create a precision site, bone die-back associated with the trauma of high-speed burning or over-zealous removal of bone in site preparation, inability of the patient's body to build new bone quickly (as a result of, for example, metabolic bone diseases), physiological barrier to exact implant placement and errors.

Attempts to address these problems have included the use of bone cement for total hip replacement. See, for example, J. Charnley, et al, "The long term reaction of bone to self-curing acrylic cement" *J. Bone Joint Surg.*, 503 822-829 (1968). In cemented arthroplasties, the cement provides initial rigid fixation and stability. However, immediate loading does not allow the prepared site the time to recover from trauma. Furthermore, cement has the complicating factor of additional chance for thermally induced necrosis as curing exotherm heat is released. A fibrous tissue layer is also commonly observed at the interface between bone and acrylic cement. Ideally, however, total bony interfaces are most desirable since a device so fixed would be able to transfer loads efficiently.

In recent years, the search for better mechanisms to increase initial stability and to minimize the occurrence of gradual loosening of prostheses has led to the development of cementless prostheses. The development of cementless prostheses, however, has led to an entirely new set of problems regarding initial stability. Cementless prostheses, must achieve their initial stability by obtaining an exact surgical press fit. Although a large number of prosthesis sizes are available, there will be areas of good contact and other areas of poor contact or gaps between the implant and the bone. This problem may be even greater in patients with osteopenic bone and at cementless revision of failed arthroplasties, which may have large bone defects.

The cementless fixation of porous-coated implants, by bony ingrowth, is also widely used, but this technique is not without associated problems. Recent investigations have shown that for bone to grow into the porous-coated implants, there must be a relatively good mating of the contact surfaces and some form of stabilization and/or patient immobilization during the initial growth phase as to prevent gross movements of the implant. Attempts have been made in the past to shorten the time required for initial implant stabilization by coating porous surfaces with calcium phosphate ceramics. However, such coatings are mechanically unstable and may dissolve under physiological conditions and, thus, the implant may become loose over a long time period. On the other hand, a good mating between implant and bone is still required in order to achieve desirable fixation.

SUMMARY OF THE INVENTION

It is an object of the invention to provide a prosthesis that results in rapid invivo formation of calcium phosphate minerals at the implant-bone interface and also encourages bone attachment to the implant when implanted in the body, thereby, providing early and strong fixation of the implant into the skeletal structure.

Another object of the invention is to provide a prosthesis with internal electrochemical facilities which results in sufficient flow of electrical current when implanted in the body, thereby, resulting in electrical stimulation of osteogenesis in close proximity of the implant.

A further object of the invention is to provide a prosthesis and a method of fixation of prostheses in bone, which overcome the disadvantages of the prior art prostheses that were intended to be permanently affixed to bone.

The invention provides a prosthetic implant for use as a body implant and for stimulating bone formation in close proximity of said implant comprising: an implantable base member having an internal housing surrounded at least partially by a conductive porous wall, said porous wall having an outer surface on which bone attachment is desired, an inner surface and a plurality of apertures extending from said inner surface through said wall to said outer surface, and adopted for tissue ingrowth when prosthetic implant is implanted in the body; a porous means located in said internal housing retaining a biocompatible electrolyte, said electrolyte being in contact with said inner surface of said porous wall; an anode also secured within said internal housing, said anode being in contact with said electrolyte; and means for electrically connecting said anode to said porous wall so as to form a galvanic couple and to generate sufficient current flow to induce invivo precipitation of calcium phosphate minerals on said outer surface of said porous wall and to stimulate bone growth into said porous wall.

DESCRIPTION OF THE PREFERRED EMBODIMENT

A more complete appreciation of the invention will be readily apparent by reference to the accompanying drawing, wherein:

FIG. 1 is a cross-sectional view of a prosthetic implant according to one embodiment of the invention; and FIG. 2 is a cross-sectional view of the implantable base member of the prosthetic implant shown in FIG. 1.

Referring to FIG. 1, there is shown a prosthetic implant intended to be permanently fixed into bone. The particular implant shown is a dental root implant, having a cylindrical shape. The prosthetic implant comprises an implantable base member 1, which may be made of a biocompatible material such as titanium or titanium-based alloys.

As shown in FIG. 2, base member 1 is provided with an internal housing 3, which is partially surrounded by a porous wall 5. The porous wall 5 has an inner surface, an outer surface and plurality of apertures 7, extending from said inner surface through said wall to said outer surface. The outer surface of the porous wall 5 is intended to form a strong bond with bone and the apertures 7 are adopted to facilitate body fluid ingress and tissue ingrowth when prosthetic implant is implanted in the body. In the preferred embodiment, the apertures 7 are provided in a uniformly spaced manner. Also, in the preferred embodiment, there are at least 20 of the apertures 7 of a generally circular cross-section and having interior diameters in the range of 50 to 300 microns. It is contemplated, however, that the diameters of the apertures could be varied or that the apertures could be formed in different geometrical shapes. The thickness of the porous wall 5 is determined by the stability from the standpoint of forming the porous wall. Roughly, however, the thickness of the porous wall ranges from 1 to 3 mm. In order to enhance the fixation of the prosthetic implant in bone, the outer surface of the porous wall 5 may have its microsurface area increased by roughening to form at least one area with crevices, irregularities, protuberances, etc., thereon. It should be understood, however, that any of the various types of porous surfaces used for fixation of parts implanted in the body may also be incorporated in the invention. For example, common porous coatings which may be incorporated in the present invention, are sintered coatings of metal particles and fibres.

As shown in FIG. 1, the prosthetic implant in this invention further comprises an anode 9 secured in the internal housing 3 and is electrically in contact with the porous wall 5. The prosthetic implant of this invention further comprises a porous means 11, placed inside the internal housing 3 for retaining a biocompatible electrolyte. The electrolyte preferably contains at least Ca- and P- bearing ions and has a pH in the range of 3 to 7. Suitable anode materials for use in this invention are alloys containing Calcium, Magnesium or a combination of these. It is also possible to use metal hydrides as the anode material. Many metals and inter metallic compounds form hydride readily because of their high affinity for hydrogen and may be used in this invention. For example, hydrogen storage alloys such as $LaNi_5$ can absorb a large amount of hydrogen and form a metal hydride which can be represented by the chemical formula $LaNi_5H_6$. Other metal hydrides which can be used are, for example, titanium hydride, magnesium hydride and $FeTiH_2$. In order to enhance the surface activity of the metal hydrides, used in this invention, it is desirable to provide a protective coating for these materials. Coatings of Palladium and Pd—Ag alloys are, in particular, beneficial for this purpose.

The porous means 11 may be made of synthetic fibers, plastics, metals, or ceramics and preferably have a porosity of about 25 percent or more, so as to permit said electrolyte to permeate through and contact both anode 9 and porous wall 5. It is particularly desirable to employ physiologically acceptable porous ceramics for this purpose. For example, porous ceramics, composed of a salt having a cation selected from the group consisting of physiologically acceptable alkali metals, alkaline earth metals and an anion selected from the group consisting of phosphate, carbonate, and silicate, may be used for this purpose. In particular, it is desirable to use a sintered porous mass of calcium phosphate ceramic for this purpose. The calcium phosphate may be selected from the group consisting of tricalcium phosphate (TCP), hydroxyapatite (HA), carbonate-containing apatite, fluro-apatite and mixtures thereof. The porous means 11 may additionally contain biologically active substances such as bone morphogenic protein (BMP), collagen and antibiotics. For example, porous means 11 may be substantially pure BMP in combination with a biodegradable porous sintered betatricalcium phosphate, and may be prepared by admixing the BMP with the porous ceramic material.

The electrolyte may be introduced into the porous means 11 by, for example, dipping the prosthetic implant in a biocompatible solution having a pH in the range of 3 to 5. It is desirable to introduce the electrolyte into the porous means 11 shortly before the prosthetic implant is implanted in the body. Alternatively, the prosthetic implant of this invention may be implanted in the body without incorporating the electrolyte. In this case, once the prosthetic implant is implanted, the body fluid in close proximity to the prosthetic implant enters the implant via apertures 7 and permeates through the porous means 11 in a relatively short period of time. The body fluid contains Ca- and P- bearing ions and has sufficient conductivity and acts as an electrolyte.

Once the electrolyte permeates through the porous means 11 and comes in contact with both anode 9 and the porous wall 5, a galvanic cell is formed in which the porous wall 5 acts as the cathode of the galvanic cell. An important reaction, taking place invivo on the porous wall 5, is the electrochemical reduction of dissolved oxygen in body fluid. As a result of this reaction, the pH, in close proximity of the porous wall 5, increases to the extent that calcium phosphate minerals precipitate on the outer surface of porous wall 5. Ca- and P- bearing ions required for invivo formation of calcium phosphate minerals are supplied by the body fluid and also originate from the interior of the prosthetic implant. The calcium phosphate minerals, formed invivo on the outer surface of the porous wall 5, eventually fill the gaps between the implant surface and the surrounding bone and results in improved implant stability, in a relatively short period of time.

The galvanic cell, formed within the prosthetic implant, further generates a small galvanic current which has beneficial stimulating effect on bone growth in close proximity of the prosthetic implant. The magnitude of the galvanic current, generated invivo, primarily, depends on the electrochemical activity and the surface area of the anode 9. It is desirable to select anodes with sufficient electrochemical activity and surface area which result in a galvanic current flow of about 20 microamperes per square centimeter of the porous wall 5. It has been known for some time that provision of a small direct current flowing to a cathode near bone will stimulate bone growth at the bone-cathode interface. The present invention, therefore, provides a prosthetic implant which electrochemically stimulates bone growth in close proximity of the implant without the need for an external power supply.

A novel prosthetic implant, for implantation in the skeletal bone and the method for making the implant which results in improved fixation and stability of the implant, has been described. While the above description of the invention has been referenced to one particular implant, it is evident that the inventive concepts described, herein, can be applied to improve stability of many types of implantable devices such as knee prostheses, intramedullary rods, hip proetheses, etc. For example, the inventive concepts of the present invention may be employed to improve stability of the femoral component of a hip prosthesis in the skeletal bone by providing an internal housing in the proximal section of the stem. The internal housing in this case is surrounded, partially, by a porous wall and is used to accomodate an anode and a porous means for retaining a biocompatible electrolyte so as to form a gelvanic couple as described above and according to the principles of this invention.

It is clear that now that the principles of the invention have been disclosed, those skilled in the art, can apply these principles to improve the stability and fixation of other implantable components. Consequently, the invention is to be construed as embracing each and every novel feature and novel combination of features within the appended claims.

The embodiments of the invention in which an exclusive property or privilege is claimed are defined as follows:

1. A prosthetic implant for use as a body implant and for stimulating bone formation in close proximity of said implant comprising:

An implantable base member consisting of an internal housing and a conductive porous wall, said porous wall surrounding said internal housing at least partially, said porous wall having an outer surface on which bone attachment is desired, an inner surface and a plurality of apertures extending from said inner surface through said wall to said outer surface, and adapted for tissue ingrowth when said prosthetic implant is implanted in the body; a porous means located in said internal housing retaining a biocompatible electrolyte, said electrolyte being in contact with said inner surface of said porous wall; an anode also secured within said internal housing, said anode being in contact with said electrolyte and means for electrically connecting said anode to said porous wall so as to form a galvanic couple and to generate sufficient current flow to induce precipitation of calcium phosphate minerals on said outer surface of said porous wall and to stimulate bone growth into said porous wall.

2. A prosthetic implant according to claim 1 wherein said implantable base member is formed of titanium or titanium-based alloys.

3. A prosthetic implant according to claim 1 wherein said outer surface of said porous wall has at least one roughened area to enhance fixation of the implant in skeletal bone.

4. A prosthetic implant according to claim 1 wherein said apertures have diameters less than 5 mm.

5. A prosthetic implant according to claim 1 wherein said anode is porous.

6. A prosthetic implant according to claim 1 wherein said anode contains calcium, magnesium and combination thereof.

7. A prosthetic implant according to claim 1 wherein said anode is made of a metal hydride charged with hydrogen.

8. A prosthetic implant according to claim 1 wherein said porous means is made of ceramic.

9. A prosthetic implant according to claim 1 wherein said porous means is made of a biocompatible calcium phosphate ceramic of the apatite group.

10. A prosthetic implant according to claim 1 wherein said porous means is made of tricalcium phosphate (TCP).

11. A prosthetic implant according to claim 1 wherein said porous means is made of a conductive material selected from the group consisting of metal hydrides charged with hydrogen and alloys containing calcium, magnesium or combination thereof.

12. A prosthetic implant according to claim 1 wherein said porous means contains biologically active substances selected from the group consisting of bone morphogenic protein (BMP), collagen and antibiotics.

13. A prosthetic implant according to claim 1 wherein said bio-compatible electrolyte contains Ca- and P- bearing ions and a pH ranging from about 3 to 8.

14. A prosthetic implant according to claim 1 wherein said implantable base member is in the form of a dental root implant.

15. A prosthetic implant according to claim 1 wherein said implantable base member is in the form of a femoral component of a hip prosthesis.

16. A prosthetic implant for permanent fixation in skeletal bone having means for rapidly inducing precipitation of calcium phosphate minerals at the interface between said implant and bone, and thereby, enhancing the stability of said implant comprising:

An implantable base member consisting of an internal housing and a conductive porous wall, said porous wall surrounding said internal housing at least partially, said porous wall having an outer surface on which bone attachment is desired, an inner surface and a plurality of apertures extending from said inner surface through said wall to said outer surface, and adapted for tissue ingrowth when said prosthetic implant is implanted in the body; a porous means located in said internal housing for absorbing and retaining body fluid when said prosthetic implant is implanted in the body; an anode also secured within internal housing and means for electrically connecting said anode to said porous wall so as to form a galvanic couple when said prosthetic implant is implanted in the body and to generate sufficient current flow to induce precipitation of calcium phosphate minerals on said outer surface of said porous wall and to stimulate bone growth into said porous wall.

* * * * *